US010837863B2

(12) United States Patent
Stanley

(10) Patent No.: US 10,837,863 B2
(45) Date of Patent: Nov. 17, 2020

(54) MASS PROPORTION SCALING APPARATUS

(71) Applicant: Ronald F. Stanley, Silver Lake, WI (US)

(72) Inventor: Ronald F. Stanley, Silver Lake, WI (US)

( * ) Notice: Subject to any disclaimer, the term of this patent is extended or adjusted under 35 U.S.C. 154(b) by 0 days.

(21) Appl. No.: 16/827,175

(22) Filed: Mar. 23, 2020

(65) Prior Publication Data

US 2020/0217747 A1  Jul. 9, 2020

Related U.S. Application Data

(63) Continuation-in-part of application No. 16/438,182, filed on Jun. 11, 2019, now Pat. No. 10,712,223.

(60) Provisional application No. 62/763,255, filed on Jun. 11, 2018, provisional application No. 62/763,412, filed on Jun. 15, 2018.

(51) Int. Cl.
| | |
|---|---|
| *G01M 1/14* | (2006.01) |
| *G01P 3/18* | (2006.01) |
| *G01M 5/00* | (2006.01) |
| *G01M 1/12* | (2006.01) |
| *G01N 33/00* | (2006.01) |

(52) U.S. Cl.
CPC ............ *G01M 5/005* (2013.01); *G01M 1/122* (2013.01); *G01M 1/14* (2013.01); *G01P 3/18* (2013.01); *G01N 2033/008* (2013.01)

(58) Field of Classification Search
None
See application file for complete search history.

(56) References Cited

U.S. PATENT DOCUMENTS

| | | | | | |
|---|---|---|---|---|---|
| 5,351,951 | A | * | 10/1994 | Hodgetts | A63B 60/42 473/409 |
| 5,528,927 | A | * | 6/1996 | Butler | A63B 53/04 73/65.03 |
| 5,616,832 | A | * | 4/1997 | Nauck | A63B 60/42 73/65.03 |
| 5,672,809 | A | * | 9/1997 | Brandt | G01N 3/52 124/65 |
| 5,703,294 | A | * | 12/1997 | McConnell | G01H 17/00 73/579 |
| 5,988,861 | A | * | 11/1999 | Baum | A63B 24/0021 702/142 |
| 6,132,326 | A | * | 10/2000 | Schweid | G01M 1/10 473/553 |
| 6,526,835 | B1 | * | 3/2003 | Hage | G01N 3/32 73/778 |
| 7,004,040 | B2 | * | 2/2006 | Johnson | G01N 3/04 73/862.636 |
| 7,415,866 | B2 | * | 8/2008 | Latiri | A63B 60/42 73/65.03 |

* cited by examiner

*Primary Examiner* — Natalie Huls
*Assistant Examiner* — Jermaine L Jenkins
(74) *Attorney, Agent, or Firm* — Dale J. Ream

(57) ABSTRACT

An apparatus to measure swing mass moments of sports' implements includes an apparatus that receive a handle of a sports' implement and measures rotational angularity thereof using a calibrated counter force element and using a static mode of measurement in association with a scale having a plurality of readings.

10 Claims, 7 Drawing Sheets

MASS PROPORTION SCALING APPARATUS

CROSS REFERENCE TO RELATED APPLICATIONS

This application claims priority to and the benefit of U.S. patent application Ser. No. 16/438,182 filed on Jun. 11, 2019 titled Mass Proportions Scaling Apparatuses which claims the benefit of U.S. Provisional Patent Application No. 62/763,255, filed Jun. 11, 2018, entitled, "Swing Mass Scale (SMS)", and of U.S. Provisional Patent Application No. 62/763,412, filed Jun. 15, 2018, entitled, "Balance Measurement Scale BMS", the content of both of which are herein incorporated by reference in their entireties.

FIELD OF THE INVENTION

The present disclosure relates to apparatuses configured to measure mass proportion characteristics of sports implements.

BACKGROUND OF THE INVENTION

Tennis players frequently measure the swing mass of their tennis rackets to ensure the racket fits the players' personal preference. Proper swinging mass proportions is essential to successful tennis play. Additionally, many tennis players own multiple rackets and need to ensure that all their rackets have identical (or nearly identical) swing mass proportions.

If the multiple rackets each has a different swing mass or proportions of mass, a player will experience degradation in his or her tennis play when switching between unmatched rackets. The majority of conventional swing mass measurements are performed by costly computer-based equipment. The cost of such equipment makes it impossible for amateur players to own and verify the swing mass of his or her rackets. Other means of swing mass measurements can be performed; however, these other swing mass measurements require complicated pendulum resonance tests that are prohibitively difficult for a player to ret up. Furthermore, this complicated test has low reliability and reproducibility and, additionally, requires the player to mathematically calculate the swing mass number.

In addition, tennis players like to determine the center mass or balance, of their rackets via a conventional balance board, which is used by laying a racket on a small od mounted on one side of a board; the racket balance is found by adjusting the racket into a perfectly horizontal and floating position, centered over the small rod. Players determine that the racket is lying horizontally by just their visual estimate. Players must read the center mass measurement from a small scale located at one end of the floating racket. This measurement has low readability due to the racket placement and movement. The low readability, in turn, yields low reliability and repeatability of results, so players currently tend to be using less than exact measurement data.

Therefore, it would be desirable to have systems and methods for players to easily and accurately determine characteristics of their tennis equipment.

SUMMARY OF THE INVENTION

According to some implementations of the present disclosure, a swing mass scale (SMS) apparatus for testing the dynamic swinging mass of sports implements, but utilizing alternative non-dynamic, static mode testing. Testing is done by measuring the tested resultant stationary angle of a pivotal arm while said arm holds a tested sports implement loaded thereto and then translating this final static arm angle test result into an equivalent dynamic test mode criteria that is then indicated on a readout scale calibrated in dynamic swing mass numbers.

Therefore, this apparatus includes a supporting base that is coupled to a pivotal beam that also centrally supports an attached pivotal arm. This arm is configured with two specially designed grips, each located offset from center of pivotal arm on its opposing distal sides. These grips will receive a user placed implement's handle (also referred to as a first portion) for testing. A calibrated counter force element is coupled between a support base and the pivotal beam that has the centrally attached pivotal arm. Thereby said counter force element is configured to oppose pivotal arm rotation (toward gravity) that will occur when placing a tested implement as a load on said arm. Furthermore, when pivotal arm is forced to rotate even further ore angular, as under higher tested loads, the counter force element will react with automatic increases of opposing force, as loaded test mass force has increased, or also when initial tested implement mass is received by pivotal arms grips, for testing.

Moreover, as tested implement mass load goes up, calibrated counter force increases to follow it up the two opposed forces on arms pivot, causing rotational seeking of torque null, or torque equality, or a minimum pivoting torque on arm, that stops all rotation, resulting in a stationary tested arm.

Again, the pivotal arm is coupled to a calibrated counter force element that will oppose any angular movement of pivotal arm, to the extent it is calibrated to do so, wherein being opposed by an implements overpowering countering mass force (toward gravity) when received upon said arm for testing. Moreover when the two countering forces (calibrated counter force element) and (implements mass/gravity load force) counter bear against the pivotal arm, this will cause instant rotation of pivotal arms angular position away from initial datum/detente stop, until these opposed forces become equalized by the process of; hen pivotal arm increases ifs angularity, this causes automatic reaction to increase the applied calibrated counter force that opposes pivotal arm rotation, until these two opposing forces finally become equalized by the arms rotated angular positional state, in response to the controlling countering forces, each one bearing against arms rotation until it stops rotating. That said, final force equalization on pivotal arm will cause a stationary arm condition ready for measurement. Here again, the pivotal arm provides a final tested relevant angle indication ready for measurement, that reflects the magnitude of tested swing mass detected during the test. Finally, the acquired stationary arm angle measurement, is conveyed by the pivotal beam coupled sensor, or pointer member, onto the readout scale.

Furthermore a measured static arm angle is translated into equivalent dynamic test mode criteria, and conveyed to a readout scale, showing a pertinent dynamic calibrated swing mass number.

In most embodiments, the pivotal arm has an initial state of preloaded force, provided by the coupled calibrated counter force element that is restrained by a detente that locates said arm at its initial incline start/stop point, or datum/zero degrees point, of the rotational testing range. And wherein arm coupled calibrated counter force element is staged, it's ready to react to further loading as tested implements mass is received upon pivotal arm for testing.

Furthermore the SMS (swing mass scale) apparatus measures dynamic swing mass of sports implements, but testing is performed, non-dynamically, in static mode.

Whereas a tested implement is user placed, into the grips of a pivotal arm for testing that cause said arm to rotate toward gravity, to the extent each specific implement load can force the pivotal arm to rotate. Whereas arm is biased with an opposing reactive calibrated counter force element that will control further angular rotation of arm, by applying a calibrated amount of increasing counter force until said arm rotation stops. Therefore the two forces have sought by counter rotating of arm, and initiated an angular state of minimal rotating torque on pivot of arm, that represents force equality. This equality causes pivotal arms angle to be stationary for measurement. This final arm angle measurement represents the swing mass magnitude of the tested implement, and is conveyed by pivotal beam coupled sensor, or pointer element, onto the support base configured readout scale, where translated into a typical dynamic mode swing mass test criterion.

In some embodiments, the implement includes any of: a bat, a tennis racket, a golf club, a racquetball racket, and a squash racket.

In some embodiments, the first portion of the implement refers to a handle of the implement.

According to some embodiments of the present disclosure, an apparatus for measuring a center of mass of an implement includes a base, a rotatable rod, a first arm, and a second arm. The rotatable rod is located at a first end of the base and is configured to pivot about its axis. The first arm is configured to guide a first portion of the implement and is configured to restrict movement of the implement over the base. The second arm includes a touch stylus and a pointer element. The touch stylus is configured to abut an end portion of the first portion of the implement when the implement is intersected by the second arm's radial movement. The pointer element is located on an end portion of the second arm.

In some embodiments, the apparatus further includes a scale. The scale includes a plurality of readings (i.e. reading indicator indicia) and is located on the base. The scale is positioned to correspond to a range of movement of the pointer element. The pointer element is configured to identify a particular reading in the plurality of readings when the touch stylus abuts the end portion of the first portion of the implement.

In some embodiments, the rotatable rod further includes an adjustment knob; rotation of the rotatable rod is controlled by the adjustment knob.

According to some embodiments of the present disclosure, an apparatus for measuring characteristics of an implement includes a base, a first arm, and a calibrated counter force element. The arm includes two grips and a supporting pivotal beam. The grips are configured to receive a handle/first portion of the implement, and the beam rotation being caused by the swing mass load of tested implement as user placed into grips of first arm. The calibrated counter force element is configured to increase its countering force as first arm becomes more angular, (toward gravity) wherein the load force of the tested implement is causing arm rotation when it's received by the arm grips for testing. Whereas the two opposition forces, (calibrated counter force element) and, (implement mass load (facing gravity)) upon first arms grips, will cause rotation and increased angularity of first arm until equalization of the two opposing forces is achieved through reactive variation of force level imposed on first arm by the calibrated counter force element that constantly reacts to the arm's rotation angle and increases opposing force if arm angularity increases away from origin datum, (detente stop), thereby causing equalization of forces on test loaded first arm. Therefore equalized forces bearing on first arm will finally cause a stationary first arm angle condition for measurement that is then conveyed by beam coupled sensor, or pointer element, to the readout scale calibrated in dynamic swing mass calibrations appropriate for testing of swinging sports implements.

According to some embodiments of the present disclosure, an apparatus for measuring characteristics of an implement includes a base, a rotatable rod, a second arm, and a third arm, a first arm with grips and beam, a calibrated counter force element. The first arm includes two grips and a centrally supporting pivotal beam. The grips are configured to receive a handle/first portion of the tested implement, and the pivotal beam is configured to couple the first arm with grips to the support base. The pivotal beam is further configured to rotate in accord with any gravitational induced torque caused by tested implements mass load as placed into the first arms grips. The calibrated counter force element is coupled to pivotal beam supporting the first arm, from the support base, and will react to any increased rotation of pivotal first arm with a counter application of increased opposition force, to impede said rotation, until the two load forces become equalized by rotated angularity of arm causing minimum rotational torque on arms pivot, or rotating null, thus stationary arm. A stationary arm angle state is then used to measure swing mass of tested implement.

The beam is configured to couple the arm with two grips to the support base. The beam supporting the first arm is further configured to pivot according to any gravitational induced torque by the tested implement loaded into the first arm. The calibrated counter force element is coupled to the first arm's support beam from the base, and configured to resist arm In some embodiments, the first portion of the implement includes a handle of the implement. In some embodiments, the implement includes any of: a bat, a tennis racket, a golf club, a racquetball racket, and a squash racket.

According to some embodiments of the present disclosure, an apparatus for measuring characteristics of an implement includes a base, a first arm, an elastic element, a rotatable rod, a second arm, and a third arm. The first arm includes a grip and a beam. The grip is configured to receive a first portion of the implement, and the beam is configured to couple the grip to the base. The beam is further configured to pivot according to a gravitational torque of the implement about the first arm. The elastic element is coupled to the first arm and the base. The elastic element is configured to be in a first configuration until the grip receives the first portion of the implement. The rotatable rod is located at a first end of the base and is configured to pivot about its axis. The second arm is configured to guide a first portion of the implement and is configured to restrict movement of the implement over the base. The third arm includes a touch stylus and a pointer element. The touch stylus is configured to abut an end portion of the first portion of the implement when the implement is intersected by the radial movement of second arm. The pointer element is located at an end portion of the third arm.

In some embodiments, the apparatus further includes a scale comprising a plurality of readings. In some examples, the apparatus further includes a scale indicator operably coupled to the arm. The scale indicator is coupled to the first arm and is further configured to identify a particular reading in the plurality of readings based on movement of the first arm. In some embodiments, the pointer element is configured to identify a particular reading in the plurality of readings When the touch stylus abuts the end portion of the first portion of the implement.

The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present invention, when taken in connection with the accompanying drawings and the appended claims.

BRIEF DESCRIPTION OF THE DRAWINGS

The accompanying drawings exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

DESCRIPTION OF THE PREFERRED EMBODIMENT

Figure 1A:
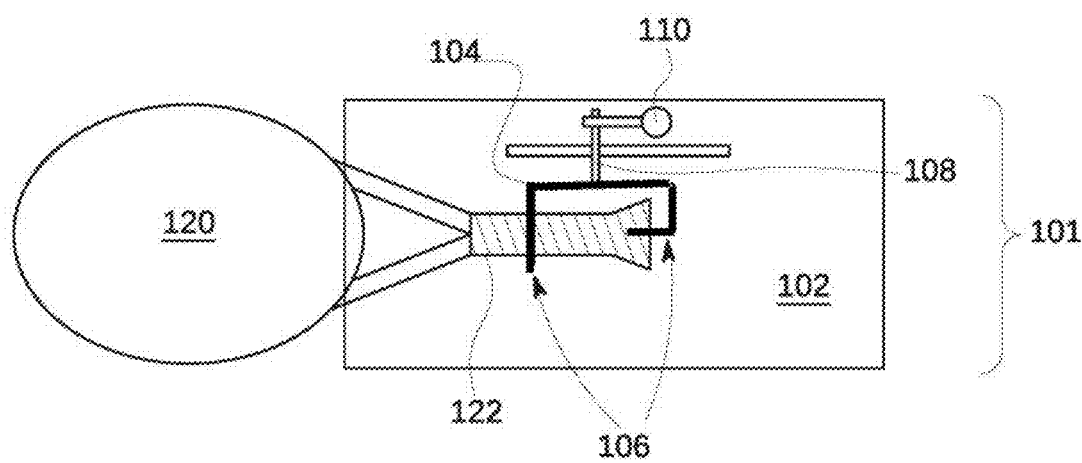
FIG. 1A shows a top view of an exemplary apparatus for measuring a swing mass moment of an implement, according to an embodiment of the present disclosure.

The present invention is described with reference to the attached figures, where like reference numerals are used throughout the figures to designate similar or equivalent elements. The figures are not drawn to scale, and are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details, or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

The present disclosure provides systems and apparatuses configured to measure characteristics of sports implements. An exemplary apparatus is configured to measure both a swing mass moment and a center of mass point of an implement and may include a base, a rotatable rod, a second arm, and a third arm, a first arm with grips and beam, and a calibrated counter force element. The first arm includes two grips and a centrally supporting pivotal beam. The grips are configured to receive a handle/first portion of the tested implement, and the pivotal beam is configured to couple the first arm with grips to the support base. The pivotal beam is further configured to rotate in accord with any gravitational induced torque caused by tested implements mass load as placed into the first arms grips. The calibrated counter force element is coupled to pivotal beam supporting the first arm, from the support base, and will react to any increased rotation of pivotal first arm with a counter application of increased opposition force, to impede said rotation, until the two load forces become equalized by rotated angularity of arm causing minimum rotational torque on arms pivot, or rotating null, thus stationary arm. A stationary arm angle state is then used to measure swing mass of tested implement.

In most examples, the pivotal arm has an initial state of preloaded force, provided by the coupled calibrated counter force element that is restrained by a detente that locates said arm at its initial incline start/stop point, or datum/zero degrees point, of the rotational testing range. And wherein arm coupled calibrated counter force element is staged, it's ready to react to further loading as tested implements mass is received upon the pivotal arm for testing.

An exemplary apparatus is configured to measure both a swing mass moment and a center of mass point of an implement. The rotatable rod is located at a first end of the base and is configured to pivot about its axis. The second arm is configured to guide a first portion of the implement and is configured to restrict movement of the implement above the base. The third arm includes a touch stylus and a pointer element. The touch stylus is configured to abut an end portion of the first portion of the implement when the implement is intersected by the radial movement of third arm. The pointer element is located at an end portion of the third arm.

Therefore, the present disclosure provides a simplified, accurate, non-computerized, and mechanical apparatus which does not require the expensive equipment of conventional measurement systems. As discussed further herein, the disclosed apparatus further provides accurate and easily attainable measurements for both a center of mass point and a swing mass moment of an implement, Additionally, although much of the present disclosure is discussed with respect to a tennis racket, any sports implement can be tested in the disclosed apparatuses, as would be readily understood by one skilled in the art. In some examples, the disclosed apparatuses measure characteristics of a golf club, a bat, a racquetball racket, a squash racket, a table tennis racket, or any other sports implement where balance or swing mass is important to success in the sport.

Figure 1B:
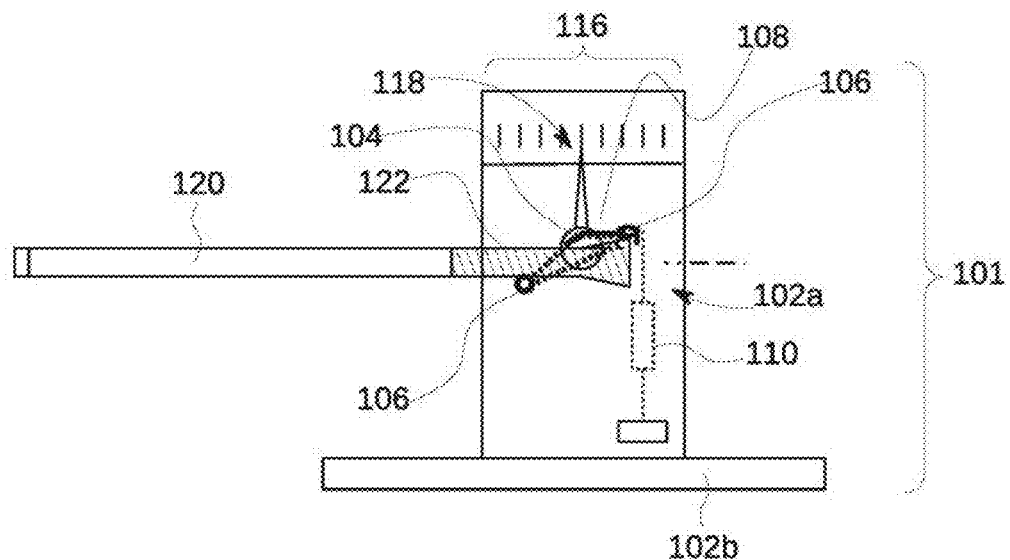
FIG. 1B shows a front view of the disclosed apparatus of FIG. 1A, according to an embodiment of the present disclosure.
Figure 1C:
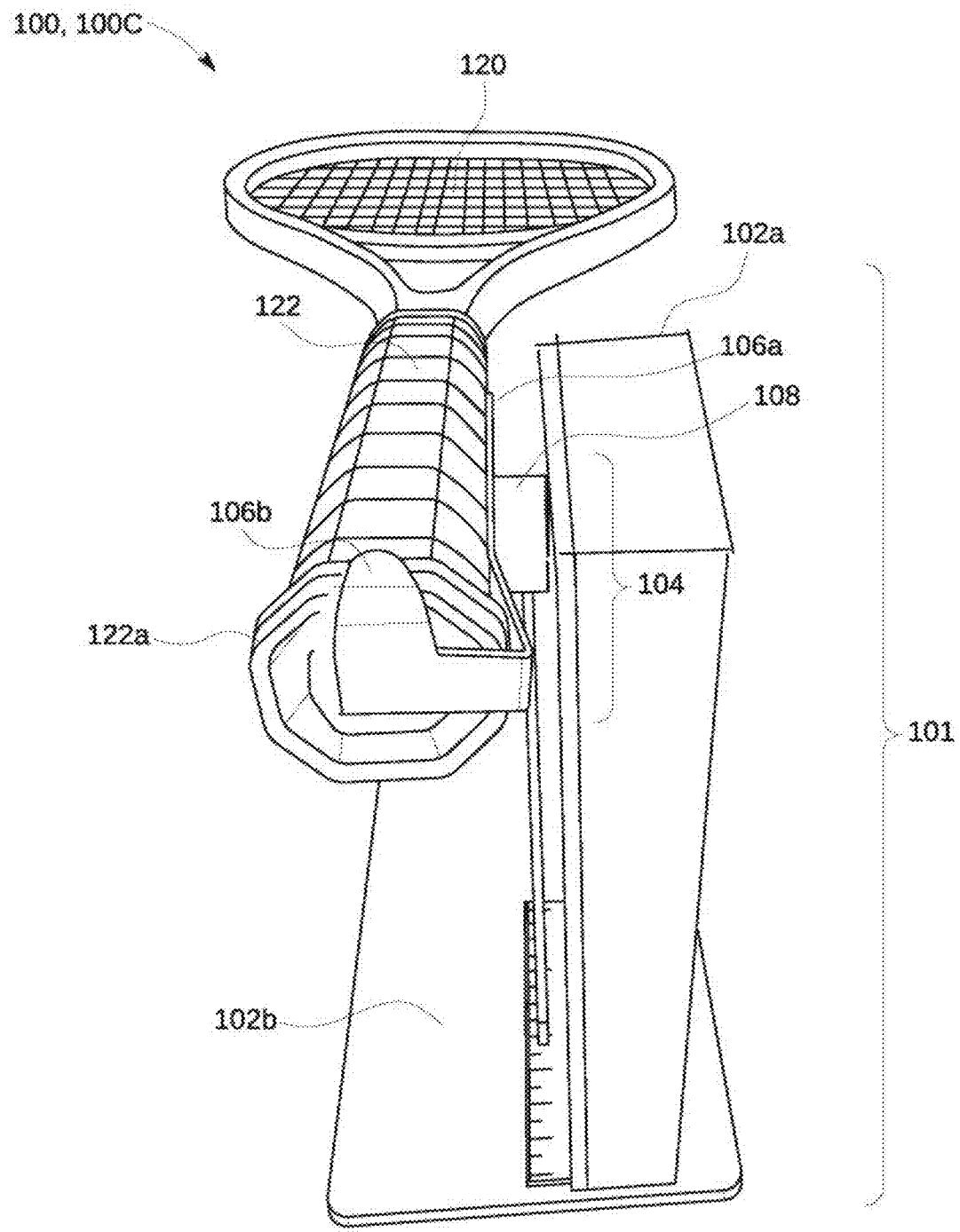
FIG. 1C shows a side view of the disclosed apparatus of FIGS. 1A and 1B, according to an embodiment of the present disclosure.

FIGS. 1A-1C show various views of a system 100 including the disclosed apparatus, shown as apparatus 101. For example, FIG. 1A shows a top view 100A, FIG. 1B shows a front view 100B, and FIG. 1C shows a side view 1000. System 100 includes an apparatus 101, a base 102, an arm 104, a grip 106, a beam 108, a calibrated counter force element 110, scale 116, scale indicator 118, implement 120, handle 122, and any combination thereof. For the purposes of the present disclosure, FIGS. 1A-1C will be discussed together to highlight various characteristics of apparatus 101.

System 100 includes an apparatus 101 and an implement 120. In some examples, implement 120 is a tennis racket. Implement 120 includes a handle 122. Apparatus 101 receives implement 120 handle portion 122 with grips 106 as configured on arm 104. Arm 104 includes grips 106 and has a centrally supporting pivotal beam 108. The grip 106 secures the handle portion 122, In some examples, the grip 106 is a c-shaped structure, a resting plate, or any other structure sufficient to hold and stabilize the implement 120. For example, as shown in FIG. 1C, the grip 106 includes a first portion 106a, attached to distal side of arm 104, which extends along a length of the handle 122, and a second portion grip 106b, which abuts an end portion 122a of the handle 122. Although not fully shown in FIG. 1C, the grip 106a is a bottom support upon which the handle 122 rests. The beam 108 centrally supports arm 104 configured having two grips 106 this said, pivotal arm assembly is coupled to a support base 102 of the apparatus 101.

included in system 100, 200, 300, but not specifically shown in FIG. 1A-1C in most examples, the pivotal arm 104 has an initial state of preloaded force provided by the coupled calibrated counter force element 110, that is restrained by a detente (not shown) against pivotal beam 108 that locates said arm 104 at its initial incline start/stop point /datum, of the rotational testing range (range typical) as scale 116. And where arm 104 is coupled to a calibrated counter force element 110 it is staged at start point incline, ready to react to further loading as tested implements 120 mass is received upon grips 106 of pivotal arm 104 for testing.

As shown in FIGS. 1B and 1C, in some examples, the base 102 is a T-shaped or U-shaped structure with a vertical portion 102a and a horizontal portion 102b. The horizontal portion 102b serves to stabilize the entire apparatus 101; in some examples, the horizontal portion 102b is weighted to withstand torque imposed on the apparatus 101 by the implement 120. The vertical portion 102a serves to keep the implement 120 secured above the horizontal portion 102b of the base 102 so that the implement 120 can pivot via the arm 104 on support beam 108 (also referred to as a beam shaft 108). The beam 108 is pivot coupled to the vertical portion 102a. For example, the beam 108 is a round shaft supported by bearings on support base, or any other pivoting mechanism, as known in the art. In some embodiments, the beam 108 is coupled via a ball and socket joint, or any other pivoting mechanism, as known in the art.

As shown in FIG. 1B, the arm 104 may be coupled to a counter force element 110. The counter force element 110 provides a varying reactive level of calibrated counter force against pivotal arm 104 rotation, whereas this calibrated counter force element 110 force magnitude is relative to a degree of pivotal arm 104 angular rotation from datum/ detente stop. Wherein a degree of pivotal arm 104 rotation is caused by a level of opposed swing mass load being presented by tested implement 120 loading is toward gravity when received after user placement onto the grips 106 of pivotal arm 104. The two forces, calibrated counter force 110 and implement 120 mass load being presented to pivotal arm 104. will by counter force interaction become equalized, and pivotal arm 104 is then stationary, after it becomes rotated to an angularity that causes calibrated counter force 110 to be of equal force magnitude to implement 120 mass load toward gravity force in opposition. The tested resultant stationary pivotal arm 104 angularity can then be measured by beam 108 pivotal angle that has a coupled sensor/pointer 118 that tests resultant angle is conveyed/projected to scale readout 116 and calibrated in dynamic swing mass.

In more detail, the arm 104 is operably coupled to a counter force elastic element 110 (the counter force). The counter force elastic element 110 serves to resist the gravitational torque exerted on the arm 104 when the arm 104 receives the implement 120 via the grips 106. The counter force element 110 is in a first configuration (e.g., an unloaded configuration) before the grip 106 of the arm 104 receives the implement 120 (e.g., before the implement is loaded for measurement). The counter force elastic element 110 is in a second configuration (e.g., a calibrated counter force loaded configuration) after the grip 106 of the arm 104 receives the implement 120 (e.g., after the implement is loaded for measurement). In some embodiments, the counter force elastic element 110 is a massive counter weight (FIG. 5), an elastic element, a spring, a magnetic force, or any other counter force element as readily contemplated by one skilled in the art.

In some examples as shown in FIG. 1B, the calibrated counter force element 110 is coupled to the base 102.

In some embodiments, the calibrated counter force element 110 is opposed to the rotation of arm 104, In other words, this calibrated force element opposes pivotal torque applied on the arm 104 (when the arm 104 has received the tested implement 120) until the arm 104 reaches an angularity that equalizes forces between (1) a torque exerted by gravitational force of the implement 120 load and (2) the calibrated counter force element 110. This equalized force results in an altered stationary angular position of the arm 104; (as moved from its original datum/detente stop position of arm 104 or position when the arm 104 has not received a test implement 120). Thus the stationary arm angle state is reached when equality of opposed forces bearing on pivotal arm 104, is reached, and therefore angle is indicative of the swing mass magnitude of the implement 120. Wherein implement 120 mass load bears downward toward gravity, when received by grips 106 on arm 104 causing rotation of arm 104 until the counter three element 110 is caused to present an equal level of counter three to prevent further arm 104 rotation. again, the calibrated counter force element 110 will increase its force as arm 104 becomes more angular away from origination point datum/detente stop, so the more massive an implement 120 is, the greater the rotation of arm 104 will be, even as opposed by increasing levels of calibrated counter force 110. Therefore the arm 104 measured final stationary angle state is being coupled to sensor indicator/pointer 118 then conveys the measured finally stationary arm 104 angle reading that is translated into an equivalent dynamic swing mass mode, appropriately calibrated, swing mass number on scale 116 located on base 102.

This as altered angle, final measurable stationary position of arm 104 is therefore different for various swing weight implements tested, and will accurately measure them based on the finally static angle of the arm 104 measured in a particular altered angular position, as rotated from its origin datum detente stop position.

In another aspect, the apparatus 101 further includes a scale 116 and a scale indicator 118. The scale includes a plurality of readings and, in some examples, is located on the vertical portion 102a of the base 102. Preferably, the scale indicator 118 is coupled to the arm 104 and is configured to indicate one of the calibration readings on the scale 116 according to a certain rotational position of the arm 104.

Movement of the scale indicator 118 is calibrated relative to the force of the calibrated counter force element 110 according to any calibration means as known in the art. For instance, the scale indicator 118 points to a specific reading on the scale 116 based on an angle of the arm 104 when the arm 104 has received the implement 120. In some examples of the present disclosure, the scale indicator 118 is coupled to the arm 104 pivot beam 108 so as to automatically point to a specific reading on the scale 116. In some examples, the scale indicator 118, therefore, identifies a dynamic swing mass of the implement 120 based on angular movement of the arm 104. For example, the scale indicator 118 can be configured to identify a particular reading on the scale 116 based on a difference in the angular position of (1) a resting position at datum/detente stop of the arm 104 (when the arm 104 has not received tested implement 120) and (2) an altered position of the arm 104 (when the arm 104 has received tested implement 120 mass load), and the arm arrived at a position of equilibrium of forces, between gravitational attraction force of the implement 120 mass load, and the opposed calibrated counter force element 110). For example, the resting stop position of the arm 104 can have an angular position of reference datum/detente stop, zero degrees. The altered position of the arm 104 can have an angular position corresponding to a swing mass reading of the implement 120, as placed in opposition on arm, to oppose calibrated counter force element 110 which is configured to constantly increase its force level if rotation of arm 104 continues to increase its angularity under implement 120 mass loading force.

More, particularly, movement of the scale indicator 118 is calibrated according to the force of the counter force (elastic) element 110, according to any calibration means as known in the art. For example, the scale indicator 118 shows a specific reading on the scale 116 based on an angle of the arm 104 when the arm 104 has received the implement 120. In some examples of the present disclosure, the scale indicator 118 is coupled to the arm 104 so as to automatically point to a specific reading on the scale 116. Although scale 116 is shown to be above the implement 120, the present disclosure contemplates that the scale 116 and the scale indicator 118 can be anywhere on the vertical portion 102a of the base 102.

In some examples, the scale indicator 118, therefore, identifies a swing mass of the implement 120 based on angular movement of the arm 104. For example, the scale indicator 118 can be configured to identify a particular reading on the scale 116 based on a difference in the angular position of (1) a resting position of the arm 104 (when the arm 104 has not received implement 120) and (2) an altered position of the arm 104 (when the arm 104 has received implement 120 and arrived at a position of equilibrium of forces, between gravitational torque of the implement 120 and the counter force elastic element 110). For example, the resting position of the arm 104 can have an angular position of reference zero degrees. The altered position of the arm 104 can have an angular position corresponding to a swing mass reading of the implement 120, when in opposition to the counter force elastic element 110.

Alternatively, the scale 116 and the sensor/scale indicator 118 are electronic devices configured to measure angular movement, of the arm 104 and pivot beam 108 and provide a swing mass reading according to pivotal arms final test angle.

In use, when apparatus 101 receives implement 120, implement 120 exerts gravitational force as pivotal torque about the arm 104. This torque causes the arm 104 to rotate until the arm 104 with the loaded implement 120 reaches an equilibrium of applied forces and becomes stationary at a new angularity; The equilibrium of forces is reached when a rotated angular position of the implement 120 upon arm 104 having a certain tested load force, is matched against the reacting increasing counter force exerted on the arm 104 by the calibrated counter force element 110, or other equivalent alternate force, within this embodiment.

Therefore, FIGS. 1A-1C show how the disclosed apparatus converts pivotal torque forces created by an implement's mass loading, when the implement is mounted on the pivotal arm 104, wherein the arm's rotation is being opposed by a calibrated counter force element. This calibrated force element opposes the arm's rotation caused by user loaded implements load force as pivotal torque until the two opposing forces become equal at a rotated new angle and a measurable stationary pivotal arm angle achieved, and conveyed by pivot beam coupled angle sensor/pointer, as a dynamic swing mass measurement on scale readout. Additional examples of system 100 are discussed further below with regards to FIG. 5.

In summary, FIGS. 1A-1C show how the disclosed apparatus converts pivotal torque created by an implement, when the implement is mounted on a pivotal arm, to a calibrated counter force element. This calibrated force element opposes the arms pivotal torque until the two opposing forces are equal and a measurable angle of the pivotal arm is reached. Additional examples of system 100 are discussed further below with regards to FIG. 5.

Figure 2A:
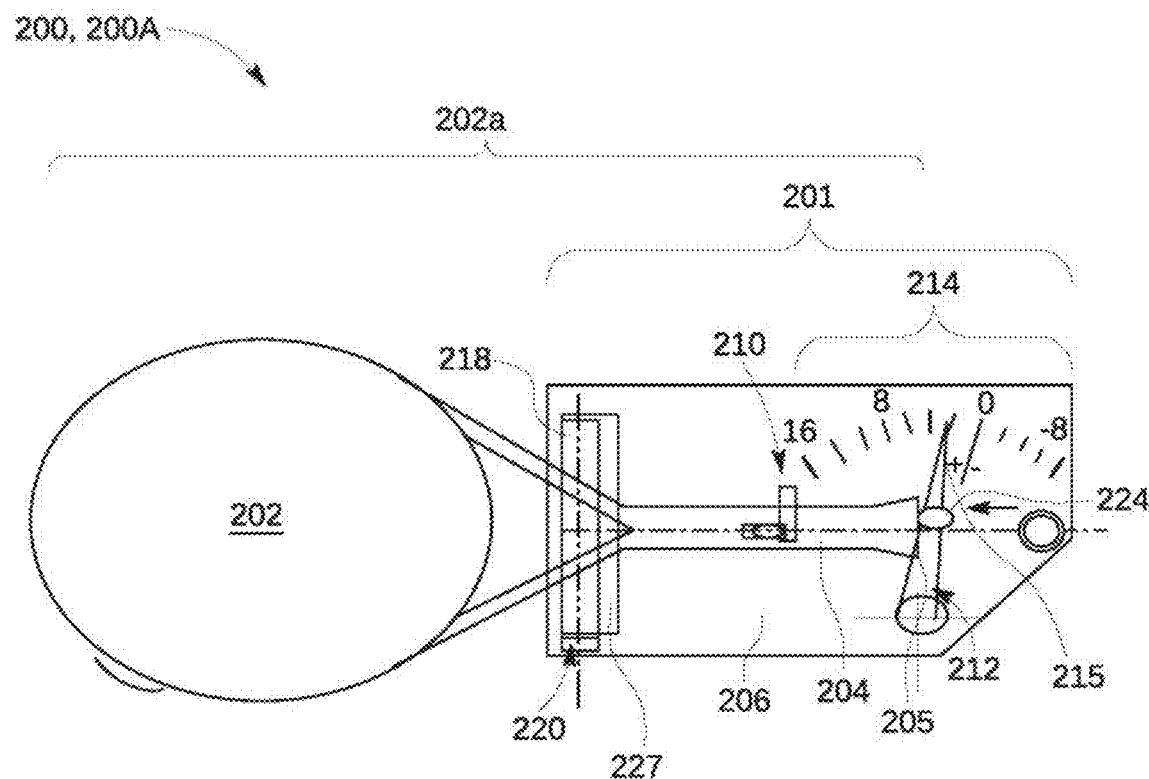
FIG. 2A shows a top view of an exemplary apparatus for measuring a center of mass point of an implement, according to an embodiment of the present disclosure.
Figure 2B:
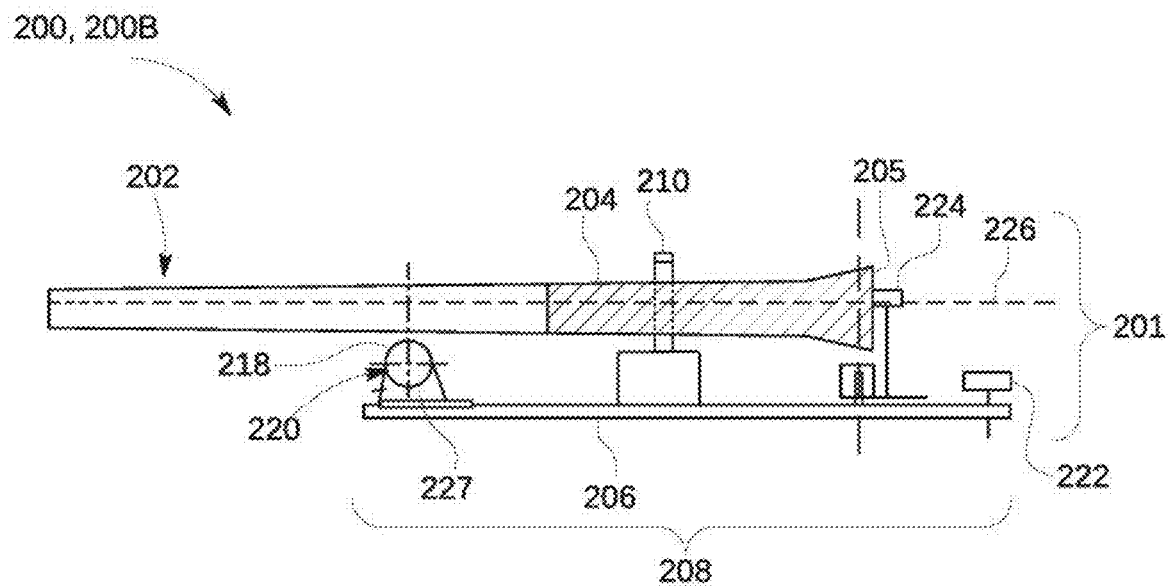
FIG. 2B shows a side view of the disclosed apparatus of FIG. 2A, according to an embodiment of the present disclosure.

FIGS. 2A-2B show various views of a disclosed apparatus configured to measure a center of mass point of an implement, shown as apparatus 200. For example, FIG. 2A shows a top view 200A, and FIG. 213 shows a side view 200B. Apparatus 200 includes an apparatus 201, implement 202, a handle 204, an end portion of the handle 205, a base 206, a base length 208, an arm 210, an arm 212, a mechanical scale 214, a rotatable rod 218, a rotatable rod support 227, an adjustment knob 220, a base adjuster 222. For the purposes of the present disclosure, FIGS. 2A and 2B will be discussed congruently to highlight various characteristics of apparatus 200.

System 200 includes an apparatus 201 and an implement 202. In some examples, implement 202 is a tennis racket. Implement 202 includes a handle 204. Implement 202 can be received by apparatus 201 by laying a middle section of the implement 202 on top of the rotatable rod 218. The adjustment knob 220 is configured to rotate axial of the rotatable rod 218 causing the implement 202 to move toward either side of the rod's 218 axial center until balanced horizontally with respect to gravity, yielding a balanced center mass position.

Figure 3:
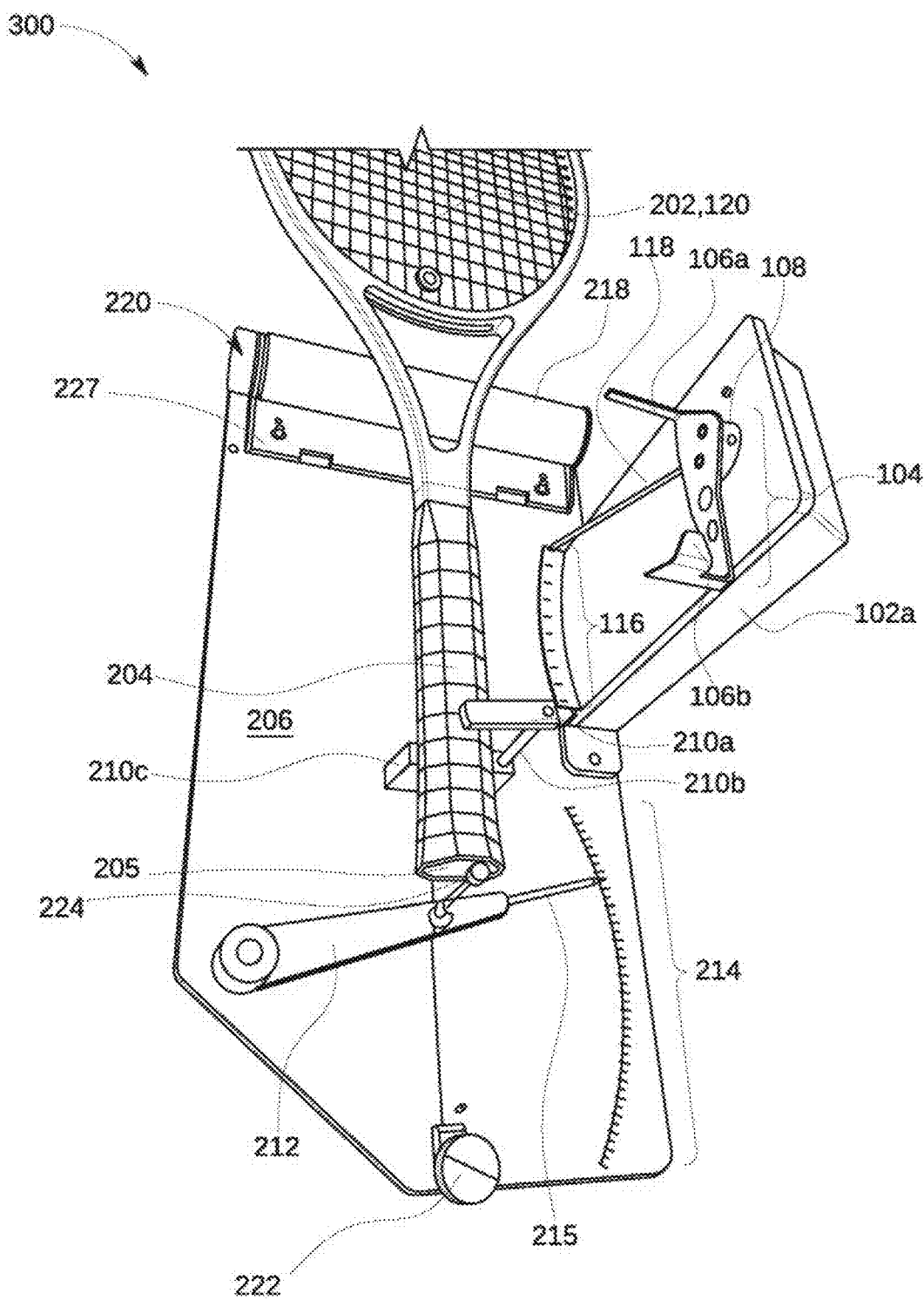
FIG. 3 shows an exemplary apparatus configured to measure a swing mass moment and a center of mass point of an implement, according to an embodiment of the present disclosure.

In some examples, shown in FIG. 2A, apparatus 201 further receives implement 202 with an arm 210, which guides and restricts the handle 204. Referring briefly to FIG. 3, in some examples, arm 210 is an L-shaped arm which attaches to the base 206. Arm 210 includes a vertical portion 210a, a horizontal portion 210b, and a base portion 210c.

(middle portion 203 of the implement 202 is raised above the base by the rotatable rod 218, as discussed further below). For example, arm 210 is an alignment retention arm or said restriction arm.

In other examples, shown in FIG. 2B, apparatus 201 further receives implement 202 with an arm 212. The arm 212 includes a touch stylus 224 and a pointer element 215. The touch stylus 224 of the arm 212 is located on the base 206 at a location adjacent to an end portion 205 of the handle 204. In some examples, a position of the touch stylus 224 is adjusted according to a length 202a of the implement 202. The shape of the touch stylus 224 can be a round rod configured to align with the end portion of first portion of implement 202 on the apparatus 201 while exerting a minimum amount of pressure against the implement 202. The arm 210 further prevents the implement 202 from moving off the rotatable rod 218 while the rotatable rod 218 is being moved by the adjustment knob 220. In some examples, the arm 210 guides the implement 202 until the implement 202 is perpendicularly centered on the rotatable rod 218.

The implement 202 aligns perpendicularly to an axis of the rotatable rod 218. Additionally, or alternatively, the implement 202 is centered over rotatable rod 218. In some instances, the rotatable rod 218 includes a support mounting 227 that is attached to base 206, allowing the rotatable rod 218 to turn freely. For example, the implement 202 will load atop rod 218, by a user. In some such instances, the rotatable rod 218 is configured as a circumferentially-rolling moving surface, allowing movement of the loaded implement 202 toward a balanced position. The rod 218 support mounting 227 is configured to move in increments on the base 206, such that the apparatus 201 can fit a plurality of implement lengths, while remaining calibrated.

Apparatus 201 further includes a rotatable rod 218 on the base 206. The rotatable rod includes an adjustment knob 220. The adjustment knob 220 is configured to move the rotatable rod 218 axially, causing circumferential movement. For example, the adjustment knob 220 rotates clockwise to move the rotatable rod 218 clockwise and rotates counter-clockwise to move the rotatable rod 218 counter-clockwise.

In some examples, the rotatable rod 218 further includes a rotatable rod support mounting 227 attached to the base 206. The support mounting allows the rotatable rod 218 to rotate freely when the implement 202 is received on top of the rotatable rod 218. In some examples, the support mounting 227 position can be adjusted relative to its initial location on the base 206 and move horizontally along a width 201 of the base 206. Therefore, system 200 can provide for receiving implements 202 of different lengths.

Therefore, when apparatus 201 has received implement 202, movement of the rotatable rod 218 adjusts whether implement 202 is balanced along a horizontal axis 226 (shown in FIG. 2B), When the implement 202 is in a balanced position, the touch stylus 224 can be moved to abut an end portion 205 (for example, a distal end) of the handle 204. The pointer element 215 of the arm 212 thus points to the scale 214, which includes a plurality of readings. The pointer element 215 identifies a particular reading in the scale 214, the particular reading corresponding to a center of mass point of the implement 202. For example, the arm 212 is configured to pivot radially so that an end portion (e.g., pointer element 215) of the arm 212 moves in a radial motion with pointer element 215 intersecting readings scale 214. In some examples, the scale 214 includes a plurality of readings which correspond to industry standard calibrations of center of mass points measured from the implement 202. For example, an apparatus 200 that is configured to measure a tennis racket includes a scale 214 with industry standard center of mass points.

Therefore, system 200 provides measurements with higher accuracy and reproducibility than conventional systems. For example, the adjustment knob 220 provides incremental shifting motion of the implement 202 laying on top of rotatable rod 218; this incremental shifting motion allows a user to easily achieve a balanced position of the implement 202. Lastly, the arm 212 is lengthy, allowing for the readings in the scale 214 to be expanded for ease of readability by the user.

FIG. 3 shows another embodiment of the present disclosure apparatus of FIGS. 1A-1C is combined with the apparatus of FIGS. 2A-2B to yield system 300. System 300 includes similar components and identical labels to systems 100 and 200 of FIGS. 1A-1C and FIGS. 2A-2B, respectively. Therefore, FIG. 3 demonstrates how an exemplary apparatus, according to an embodiment of the present disclosure, is configured to measure both a swing mass moment and a center of mass point of an implement. Additionally, although a tennis racket is shown as the implement 120 and 202 of FIGS. 1A-3, the present disclosure contemplates that any implement can be tested, as would be readily contemplated by one skilled in the art. Exemplary implements include baseball bats, softball bats, table tennis rackets, racquetball rackets, squash rackets, golf clubs, tennis rackets, and any other elongated sports implement, as known in the art.

Figure 4:
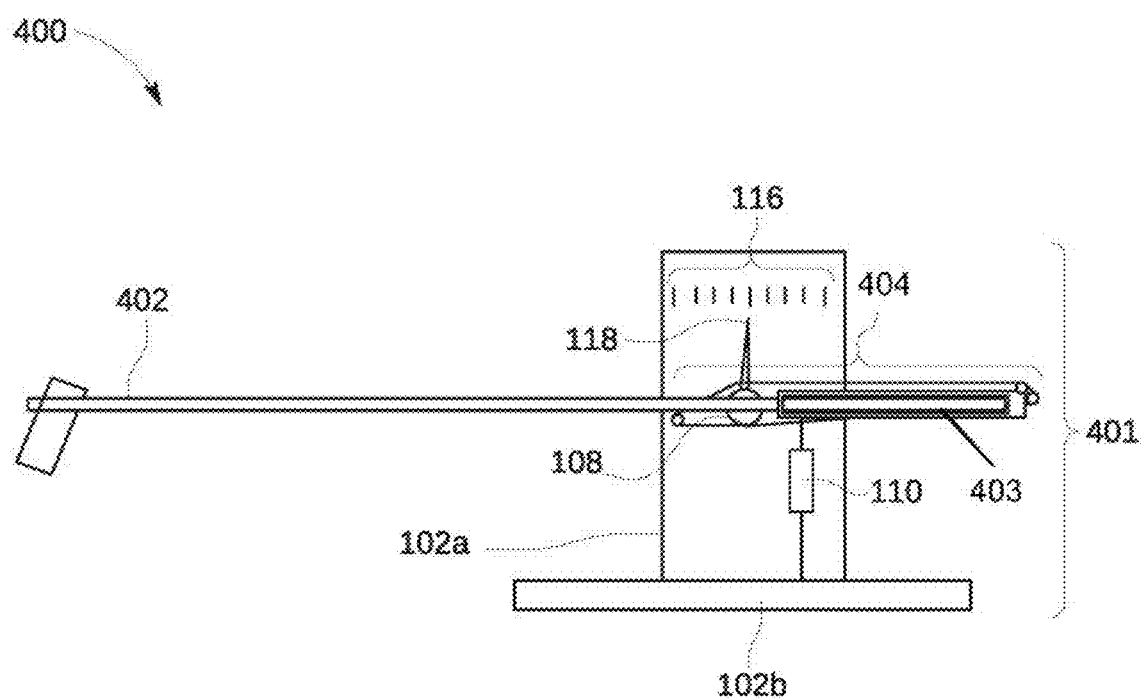
FIG. 4 shows an exemplary apparatus configured to measure a swing mass moment of a golf club, according to an embodiment of the present disclosure.

FIG. 4 shows an exemplary system 400 which includes an apparatus 401 and a golf club 402. Apparatus 401 contains similar elements to apparatus 101 of FIGS. 1A-1C. An arm portion 404 is further receives the golf club 402. Arm portion 404 is modified as compared to arm 104 of FIGS. 1A-1C because a handle 403 of the golf club 402 is longer than a handle portion of a tennis racket. Therefore, FIG. 4 demonstrates how the disclosed apparatus can be modified to accommodate dimensions of different implements. As readily contemplated by a person skilled in the art, arm portion 404 can be further modified to receive another sports implement, including, for example, baseball bats, softball bats, table tennis rackets, racquetball rackets, squash rackets, and any other elongated sports implement, as known in the art.

Figure 6A:
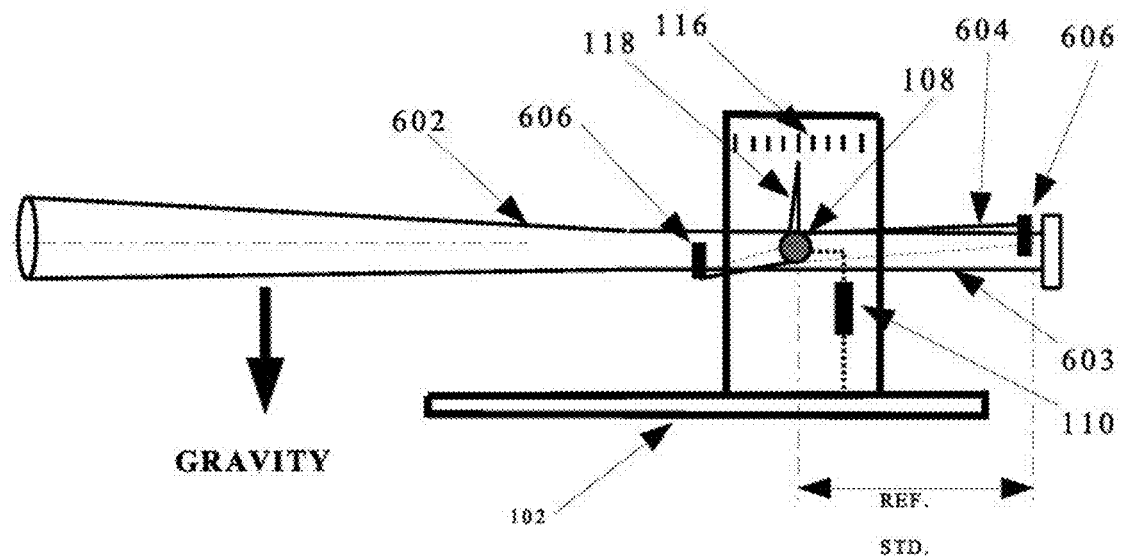
FIGS. 6A-6B show an exemplary apparatus configured to measure a swing mass moment of a ball bat, according to an embodiment of the present disclosure.
Figure 6B:
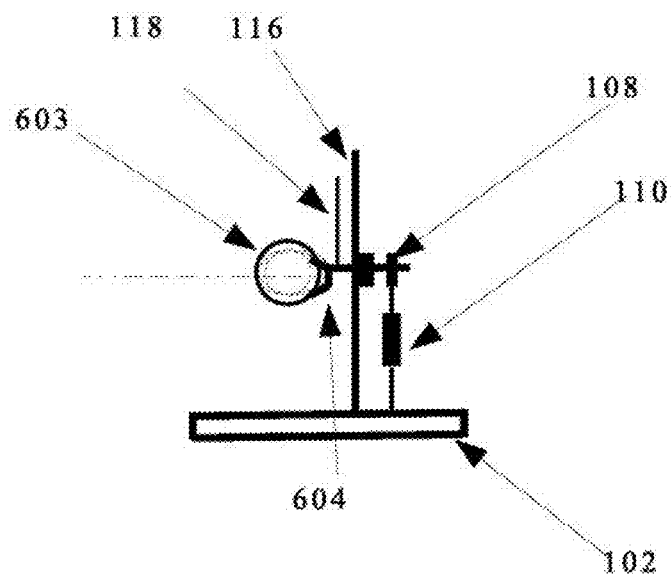

FIG. 6 shows an exemplary system 600 which includes an apparatus 601 and a ball bat 602. Apparatus 601 contains similar elements to apparatus 101 of FIG. 1A. A pivotal arm portion 604 configured with grips 606 further receives the ball bat 602. Arm portion 604 is modified as compared to arm 104 of FIG. 1A because a handle 603 of the ball bat 602 is longer than a handle portion of a tennis racket. Therefore, FIG. 6 demonstrates how the disclosed apparatus can be modified to accommodate dimensions of different implements. As readily contemplated by a person skilled in the art, arm portion 604 can be further modified to receive another sports implement, including, for example, table tennis rackets, racquetball rackets, squash rackets, and any other elongated sports implement, as known in the art.

ADDITIONAL EMBODIMENTS

Figure 5:
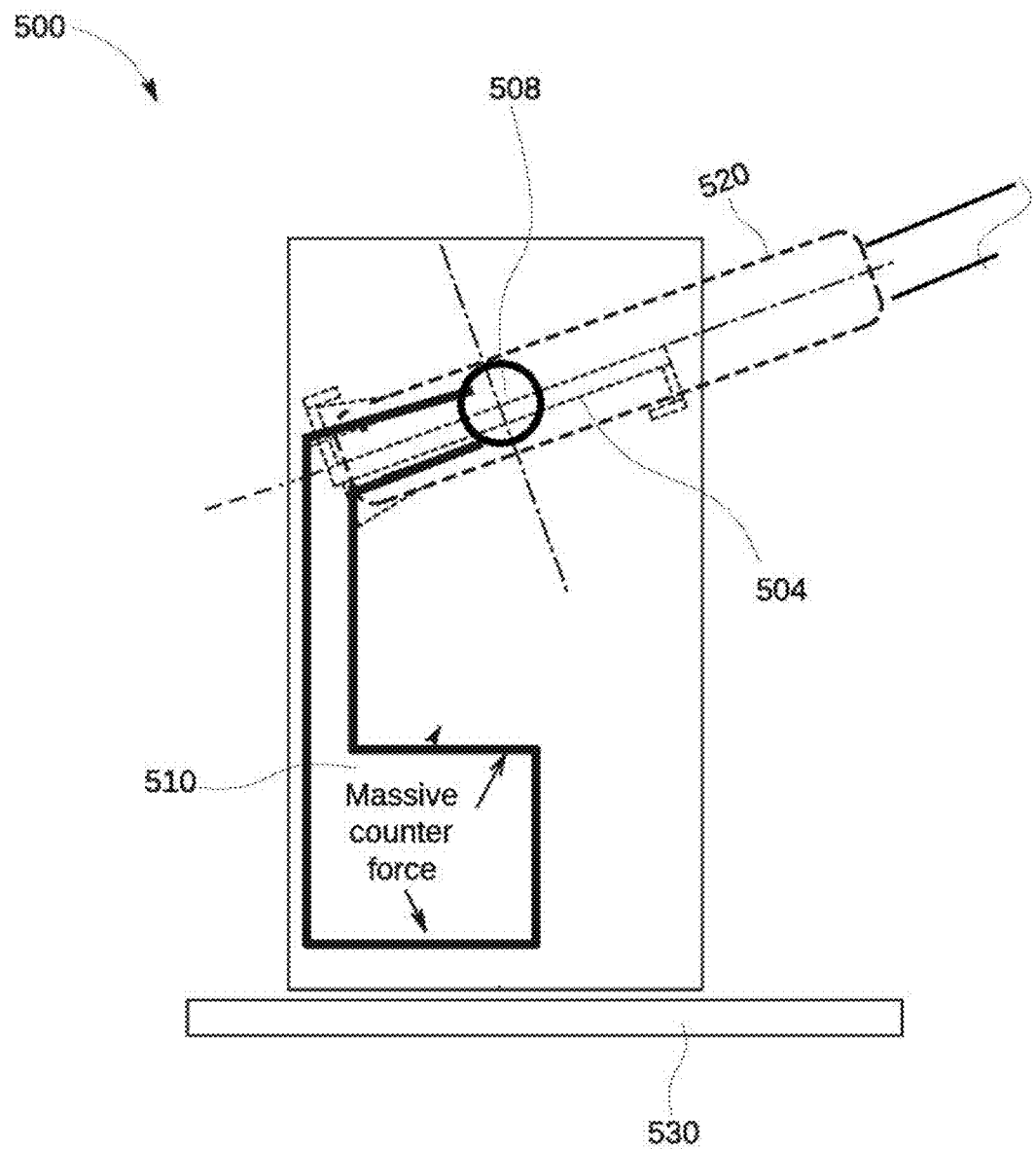
FIG. 5 illustrates an alternative embodiment of the disclosed apparatus of FIG. 1B, according to an embodiment of the present disclosure.

In some embodiments of the present disclosure, other mechanical mechanisms can be used to provide counter force to oppose the gravitational torque force imposed by tested implement upon arm 104 (as shown in FIGS. 1A-1C). For example, in one exemplary embodiment of the present disclosure as shown in FIG. 5, a massive counterweight element can be used. FIG. 5 shows an apparatus 500 which includes the elements that are the same as, or similar to, FIGS. 1A-1C, except that in FIG. 5, the massive counterweight element 510 is used in place of calibrated counter force element 110. In FIG. 5, like reference numerals are used to designate similar or equivalent elements of FIGS. 1A-1C. Therefore, FIG. 5 shows how the massive counterweight element 510 can be coupled to the pivoting support beam of the arm 504 to oppose gravitational torque exerted on the arm 504 by an implement 520. The massive counterweight element 510 can be attached to the pivot beam 508, coupled to pivotal arm 504, supported by base 520.

What is claimed is:

1. An apparatus for measuring a swing mass moment of a sports' implement, comprising:
    a support base having a horizontal portion and a vertical portion extending upwardly from said horizontal portion;
    an arm having opposed ends and a pair of grips coupled to said opposed ends, respectively, said pair of grips being configured to receive a first portion of the sports' implement;
    wherein said arm includes a beam pivotally coupling said arm to said vertical portion of said base, said beam being configured to pivot according to a gravitational torque of the sports' implement about the arm;
    a calibrated counter force element coupled to said arm between said support base and said beam and that is configured to apply an automatically increasing amount of counter force against an increase in angular rotation that is applied to said arm;
    wherein said calibrated counterforce element is movable between a first unloaded configuration before the sports' implement is received by said pair of grips and a second loaded configuration after the sports' implement is received by said pair of grips;
    a scale positioned on said vertical portion of said base and having a plurality of reading indicators indicative of measurements of a dynamic swinging mass of the sports implement using static assessment criteria; and
    a scale indicator coupled to said arm and mechanically connected to said scale and configured to mechanically indicate a respective reading indicator associated with a static angle of said arm.

2. The apparatus as in claim 1, wherein the sports' implement is one of a bat, a tennis racket, a golf club, a racquetball racket or a squash racket.

3. The apparatus as in claim 2, wherein said first portion of the sports' implement is a handle.

4. The apparatus as in claim 1, wherein said calibrated counter force element includes an elastic member.

5. The apparatus as in claim 4, wherein said elastic member is a spring.

6. The apparatus as in claim 1, wherein said calibrated counter force element is a massive counter force member.

7. The apparatus as in claim 1, wherein said scale is configured to measure dynamic swinging mass of sports implements using static assessment criteria.

8. The apparatus as in claim 1, wherein:
    said pivotal arm has an initial configured angular state with a preloaded calibrated counter force that is held restrained by a detente that positions said pivotal arm at an initial incline start/stop datum;
    said beam is coupled to said calibrated counter force element and to said support base and operable to apply opposing force against rotation of said pivotal arm.

9. The apparatus as in claim 1, wherein:
    said calibrated counter force element automatically graduates a counter force level to a force level caused by a rotation of said pivotal arm until equalized forces are experienced on said pivotal arm; and
    said equalized forces on said pivotal arm causes a stationary measurable arm angle condition that is static and shown on said scale and indicative of a dynamic swing test calibration.

10. The apparatus as in claim 1, further comprising a touch stylus configured to abut an end portion of the first portion of the sports' implement when the sports' implement is intersected by radial movement of said pivotal arm.

* * * * *